United States Patent
Pedain et al.

(10) Patent No.: US 10,195,614 B2
(45) Date of Patent: Feb. 5, 2019

(54) COMPOSITION OF FATTY ACIDS AND N-ACYL DERIVATIVES OF SARCOSINE FOR THE IMPROVED FLOTATION OF NONSULFIDE MINERALS

(71) Applicant: Clariant International Ltd., Muttenz (CH)

(72) Inventors: Klaus-Ulrich Pedain, Dietzenbach-Steinberg (DE); Jesús Pitarch López, Frankfurt am Main (DE); Gunter Lipowsky, Ladenburg (DE); Jacques Collin Bezuidenhout, Frankfurt (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 15/562,830

(22) PCT Filed: Mar. 1, 2016

(86) PCT No.: PCT/EP2016/054291
§ 371 (c)(1),
(2) Date: Sep. 28, 2017

(87) PCT Pub. No.: WO2016/155966
PCT Pub. Date: Oct. 6, 2016

(65) Prior Publication Data
US 2018/0104701 A1 Apr. 19, 2018

(30) Foreign Application Priority Data
Mar. 30, 2015 (EP) .................... 15000927

(51) Int. Cl.
| B03D 1/02 | (2006.01) |
| B03D 1/008 | (2006.01) |
| B03D 1/01 | (2006.01) |
| C07C 53/126 | (2006.01) |
| C07C 233/05 | (2006.01) |

(52) U.S. Cl.
CPC ............... *B03D 1/008* (2013.01); *B03D 1/01* (2013.01); *B03D 1/021* (2013.01); *C07C 53/126* (2013.01); *C07C 233/05* (2013.01); *B03D 2201/005* (2013.01); *B03D 2201/02* (2013.01); *B03D 2203/04* (2013.01); *B03D 2203/06* (2013.01)

(58) Field of Classification Search
None
See application file for complete search history.

(56) References Cited

U.S. PATENT DOCUMENTS

| 4,514,290 A * | 4/1985 | Swiatkowski ............ B03D 1/01 209/166 |
| 4,612,112 A * | 9/1986 | Swiatkowski ............ B03D 1/01 209/166 |
| 5,147,528 A | 9/1992 | Bulatovic |
| 2015/0238976 A1 * | 8/2015 | Da Silva ................ B03D 1/008 209/4 |

FOREIGN PATENT DOCUMENTS

| DE | 1146824 | 4/1963 |
| DE | 300730 | 7/1992 |
| EP | 2708282 | 3/2014 |
| WO | WO2014040686 | 3/2014 |

OTHER PUBLICATIONS

International Search Report for PCT/EP2016/054291, dated May 9, 2016.
International Preliminary Report on Patentability for PCT/EP2016/054291, dated Oct. 3, 2017.
Machine translation of DD300730, Jul. 16, 1992.
Machine translation of DE 1146824, Apr. 11, 1963.
"Fatty Acid Composition by Gas Chromatography", AOCS Official Methods, American Oil Chemists Society, (2005).

* cited by examiner

*Primary Examiner* — Thomas M Lithgow
(74) *Attorney, Agent, or Firm* — Tod A. Waldrop

(57) ABSTRACT

This invention relates to a collector composition for the direct froth flotation of nonsulfide ores comprising
a) 50-99 wt.-% of a mixture of fatty acids and
b) 1-50 wt.-% of an N-acyl derivative of sarcosine of the formula (I)

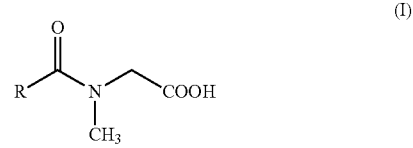

(I)

wherein
R is a saturated or unsaturated hydrocarbon chain with 7 to 21 carbon atoms, wherein the mixture of comprises 10.0-35.0 wt.-% of fatty acid having a saturated $C_{11}$ hydrocarbon group, 2.5-15.0 wt.-% of fatty acid having a saturated $C_{13}$ hydrocarbon group, 10.0-25.0 wt.-% fatty acid having a monounsaturated $C_{17}$ hydrocarbon group and 20.0-45.0 wt.-% fatty acid having a bisunsaturated $C_{17}$ hydrocarbon group.

10 Claims, No Drawings

COMPOSITION OF FATTY ACIDS AND N-ACYL DERIVATIVES OF SARCOSINE FOR THE IMPROVED FLOTATION OF NONSULFIDE MINERALS

This invention relates to a novel collector composition comprising a mixture of at least two fatty acids and at least one N-acyl derivative of sarcosine and its use in the direct froth flotation of nonsulfide minerals. The use of the novel collector composition provides improved flotation efficiency.

Froth flotation is a physico-chemical process used to separate mineral particles considered economically valuable from those considered waste. It is based on the ability of air bubbles to selectively attach onto those particles previously rendered hydrophobic. The particle-bubble combinations then rise to the froth phase from where it discharges the flotation cell whilst the hydrophilic particles remain in the flotation cell. Particle hydrophobicity is, in turn, induced by special chemicals called collectors. In direct flotation systems, it is the economically valuable minerals which are rendered hydrophobic by the action of the collector. Similarly, in reverse flotation systems, the collector renders hydrophobicity to those mineral particles considered waste. The efficiency of the separation process is quantified in terms of recovery and grade. Recovery refers to the percentage of valuable product contained in the ore that is removed into the concentrate stream after flotation. Grade refers to the percentage of the economically valuable product in the concentrate after flotation. A higher value of recovery or grade indicates a more efficient flotation system.

The use of mixtures of fatty acids and sarcosine derivatives for the froth flotation of nonsulfide minerals is well-known.

In DD-300730 the use of a collector composition for the froth flotation of fluorite comprising an N-acyl derivative of sarcosine and a saturated or unsaturated fatty acid having a hydrocarbon chain with 14 to 24 carbon atoms is described.

In U.S. Pat. No. 5,147,528 a process for the direct flotation of phosphate is described where an oxidized intimate mixture of a fatty acid containing 12 to 36 carbon atoms, a tall oil pitch, an amine derived from a plant, sarcosine and a fuel oil or furnace oil is used as collector.

U.S. Pat. No. 4,514,290 describes a collector composition comprising a fatty acid or salt thereof, an amidocarboxylic acid or amidosulfonic acid containing an organic hydrophobic group, or a salt thereof, and a partial ester of phosphoric acid and at least one alkoxylated alcohol. Such composition is claimed to show improved efficiency for the froth flotation of minerals containing alkaline earth metals, such as apatite, scheelite, magnesite and barite. The fatty acid in the preferred compositions has 14 to 22 carbon atoms.

WO-2014040686 describes a flotation agent for phosphate ore, comprising at least one fatty acid and at least one N-acyl derivative of sarcosine.

The present invention is related to a novel collector composition comprising a mixture of at least two fatty acids and at least one N-acyl derivative of sarcosine and its use for the beneficiation of nonsulfide minerals. The composition of at least two fatty acids and at least one N-acyl derivative according to the present invention affords in comparison to the collector compositions described by the state-of-the-art an improvement of the flotation efficiency. Under improved flotation efficiency is meant that higher mineral recovery and/or purity are achieved. Furthermore, the collector composition according to the present invention is very easy to prepare by simply mixing and not require any additional treatment, like for example an oxidation step, in order to show excellent improvement of the flotation efficiency.

Unexpectedly it was found that a composition containing 50-99 wt.-% of a mixture of at least two fatty acids and 1-50 wt.-% of an N-acyl derivative of sarcosine show improved flotation of nonsulfide minerals expressed in terms of higher mineral recovery and/or higher purity.

The instant invention therefore relates to a collector composition comprising
a) 50-99 wt.-% of a mixture of fatty acids and
b) 1-50 wt.-% of an N-acyl derivative of sarcosine of the formula (I)

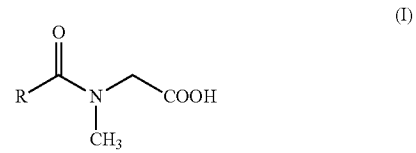

wherein
R is a saturated or unsaturated hydrocarbon chain with 7 to 21 carbon atoms, wherein the mixture of fatty acids comprises 10.0-35.0 wt.-% of fatty acid having a saturated $C_{11}$ hydrocarbon group, 2.5-15.0 wt.-% of fatty acid having a saturated $C_{13}$ hydrocarbon group, 10.0-25.0 wt.-% fatty acid having a monounsaturated $C_{17}$ hydrocarbon group and 20.0-45.0 wt.-% fatty acid having a bisunsaturated $C_{17}$ hydrocarbon group.

The inventive collector composition may comprise other fatty acids to balance to 100 wt.-%. The weight percentages refer to the total fatty acid content of the inventive collector composition as being 100 wt.-%.

In a preferred embodiment the mixture of fatty acids comprises fatty acids having
1.0-6.5 wt.-% of saturated $C_7$
1.0-4.0 wt.-% of saturated $C_9$
10.0-35.0 wt.-% of saturated $C_{11}$
2.5-15.0 wt.-% of saturated $C_{13}$
1.0-7.0 wt.-% of saturated $C_{15}$
0.0-1.0 wt.-% of monounsaturated $C_{15}$
0.0-1.0 wt.-% of bisunsaturated $C_{15}$
0.5-2.0 wt.-% of saturated $C_{17}$
10.0-25.0 wt.-% of monounsaturated $C_{17}$
20.0-45.0 wt.-% bisunsaturated $C_{17}$
0.0-2.0 wt.-% trisunsaturated $C_{17}$
0.0-1.0 wt.-% saturated $C_{19}$
0.0-4.0 wt.-% monounsaturated $C_{19}$ hydrocarbon chains, and
0.0-7.0 wt.-% other fatty acids The expression "saturated hydrocarbon chain" means preferably alkyl groups. The expression "monosaturated hydrocarbon chain" means preferably alkenyl groups. The expression "bisunsaturated hydrocarbon chains" means alkenyl groups having two double bonds.

Fatty acids are defined in the sense of this invention as mixtures of carboxylic acids bearing a long linear hydrocarbon chain, which can be saturated or unsaturated or multiply unsaturated. Especially effective for the scope of this invention is the use of fatty acids from vegetable oils and tall oil fatty acids. The preferred fatty acids in the sense of this invention are coconut oil fatty acid and tall oil fatty acid. Predominant carboxylic acids in the coconut oil fatty acid are lauric acid (saturated $C_{11}$ hydrocarbon chain) with a content between 44 and 54 wt.-% and myristic acid (saturated $C_{13}$ hydrocarbon chain) with a content between 13 and 20 wt.-%. The preferred quality of tall oil fatty acid has an acid value higher than 190 mg KOH/g and a content of rosin acids and unsaponifiables lower than 2.1 wt.-% and 2.0 wt.-%, respectively. Predominant carboxylic acids in the tall oil fatty acid are oleic acid (monounsaturated $C_{17}$ hydrocarbon chain) with a content between 25 and 50 wt.-% and linoleic acid (bisunsaturated $C_{17}$ hydrocarbon chain) with a content between 35 and 60 wt.-%.

The characterization of the alkyl chain distribution in fatty acids can be done via gas chromatography after conversion of the carboxylic acids in the volatile methyl ester derivatives according to the AOCS Method Ce 1-62, "Fatty Acid Composition by Gas Chromatography" AOCS Official Methods (2005) American Oil Chemists Society.

The mixtures of fatty acids which are especially effective in the collector compositions according to the present invention contain between 0.3 and 1.7 weight parts of fatty acids from vegetable oils to 1 weight part of tall oil fatty acid. The most preferred ratio for the mixture of fatty acids according to this invention is 1 weight part of coconut oil fatty acid to 1 weight part of tall oil fatty acid.

Especially preferred are N-acyl derivatives of sarcosine where R is a saturated or unsaturated hydrocarbon chain with 11 to 19 carbon atoms. The most preferred N-acyl derivative of sarcosine is N-oleoylsarcosine.

Especially preferred collector compositions according to the present invention contain 65-99 wt.-% of a mixture of fatty acids (component a) and 1-35 wt.-% of an N-acyl derivative of sarcosine (component b). Most preferred collector compositions contain 80 wt.-% of a 1:1 weight mixture of coconut oil fatty acid and tall oil fatty acid and 20 wt.-% of N-oleoylsarcosine.

The composition of the invention is for use as collector in direct froth flotation processes of nonsulfide ores. It was found that the composition of the invention is especially suitable for the direct froth flotation of nonsulfide ores containing alkaline earth metals, as apatite, calcite, scheelite, fluorspar, magnesite and barite. Most surprisingly it was found that the composition of the invention is also especially suitable for the direct froth flotation of ilmenite, a titanium-iron oxide mineral of formula $FeTiO_3$ which is the most important source for titanium.

Furthermore, the present invention also relates to a process for beneficiation of nonsulfide minerals, the process comprising the steps of bringing the collector composition according to the present invention in contact with an aqueous suspension of the nonsulfide mineral and frothing the so formed mineral pulp. The collector composition according to the present invention is preferably used in amounts between 100 and 1000 g/t of solid ore for the direct froth flotation of nonsulfide ore. It is also possible to add other flotation reagents to the mineral pulp, if these are required. Examples of these reagents are frothers as for example pine oil, polyglycols, polyoxyparaffins or alcohols, depressants as for example starch, carboxymethylcellulose or sodium silicate and pH-regulators as for example sodium hydroxide or sodium carbonate.

EXAMPLES

1. General Procedure for Preparation of Collector Compositions According to this Invention:

Distilled coconut fatty acid sample was warmed to 35° C. until it was entirely melted and then added to tall oil fatty acid at room temperature. The fatty acid mixture was then homogenised by a slow stirring action. Finally, N-oleoylsarcosine was slowly added to the fatty acid mixture. The mixture was thereafter homogenised for a further 10 minutes. The procedure is completed when a clear, yellow-coloured liquid solution is obtained.

2. Collector Compositions According to this Invention Prepared Following Used the Procedure Describer Under 1.

Composition 1:
Component a:
80 wt.-% of a mixture of 1 weight part of distilled coconut fatty acid and 1 weight part of tall oil fatty acid with a hydrocarbon chain distribution as follows:
3.25 wt.-% of saturated $C_7$ hydrocarbon chain
2.85 wt.-% of saturated $C_9$
25.65 wt.-% of saturated $C_{11}$
8.60 wt.-% of saturated $C_{13}$
4.45 wt.-% of saturated $C_{15}$
0.02 wt.-% of monounsaturated $C_{15}$
0.20 wt.-% of bisunsaturated $C_{15}$
1.25 wt.-% of saturated $C_{17}$
19.10 wt.-% of monounsaturated $C_{17}$
28.5 wt.-% bisunsaturated $C_{17}$
0.60 wt.-% trisunsaturated $C_{17}$
0.05 wt.-% saturated $C_{19}$
1.25 wt.-% monounsaturated $C_{19}$
4.3 wt.-% others
Component b:
20 wt.-% N-oleoylsarcosine Composition 2:
Component a:
80 wt.-% of a mixture of 0.33 weight part of distilled coconut fatty acid and 1 weight part of tall oil fatty acid with a hydrocarbon chain distribution as follows:
1.62 wt.-% of saturated $C_7$ hydrocarbon chain
1.42 wt.-% of saturated $C_9$
12.82 wt.-% of saturated $C_{11}$
4.30 wt.-% of saturated $C_{13}$
2.37 wt.-% of saturated $C_{15}$
0.04 wt.-% of monounsaturated $C_{15}$
0.30 wt.-% of bisunsaturated $C_{15}$
1.17 wt.-% of saturated $C_{17}$
24.70 wt.-% of monounsaturated $C_{17}$
42.15 wt.-% bisunsaturated $C_{17}$
0.90 wt.-% trisunsaturated $C_{17}$
0.02 wt.-% saturated $C_{19}$
1.87 wt.-% monounsaturated $C_{19}$
6.40 wt.-% others
Component b:
20 wt.-% N-oleoylsarcosine Composition 3:
Component a:
80 wt.-% of a mixture of 1.66 weight part of distilled coconut fatty acid and 1 weight part of tall oil fatty acid with a hydrocarbon chain distribution as follows:
4.10 wt.-% of saturated $C_7$ hydrocarbon chain
3.59 wt.-% of saturated $C_9$
32.32 wt.-% of saturated $C_{11}$
10.84 wt.-% of saturated $C_{13}$
5.53 wt.-% of saturated $C_{15}$
0.02 wt.-% of monounsaturated $C_{15}$
0.15 wt.-% of bisunsaturated $C_{15}$
1.29 wt.-% of saturated $C_{17}$
16.19 wt.-% of monounsaturated $C_{17}$
21.40 wt.-% bisunsaturated $C_{17}$
0.44 wt.-% trisunsaturated $C_{17}$
0.06 wt.-% saturated $C_{19}$
0.92 wt.-% monounsaturated $C_{19}$
3.21 wt.-% others Component b:
20 wt.-% N-oleoylsarcosine
Composition 4:
Component a:
67 wt.-% of a mixture of 1 weight part of distilled coconut fatty acid and 1 weight part of tall oil fatty acid with a hydrocarbon chain distribution as follows:
3.25 wt.-% of saturated $C_7$ hydrocarbon chain
2.85 wt.-% of saturated $C_9$
25.65 wt.-% of saturated $C_{11}$
8.60 wt.-% of saturated $C_{13}$
4.45 wt.-% of saturated $C_{15}$
0.02 wt.-% of monounsaturated $C_{15}$
0.20 wt.-% of bisunsaturated $C_{15}$
1.25 wt.-% of saturated $C_{17}$
19.10 wt.-% of monounsaturated $C_{17}$
28.5 wt.-% bisunsaturated $C_{15}$
0.60 wt.-% trisunsaturated $C_{17}$
0.05 wt.-% saturated $C_{19}$
1.25 wt.-% monounsaturated $C_{19}$
4.3 wt.-% others
Component b:
33 wt.-% N-oleoylsarcosine
Composition 5:
Component a:
75 wt.-% of a mixture of 1 weight part of distilled coconut fatty acid and 1 weight part of tall oil fatty acid with a hydrocarbon chain distribution as follows:
3.25 wt.-% of saturated $C_7$ hydrocarbon chain
2.85 wt.-% of saturated $C_9$
25.65 wt.-% of saturated $C_{11}$
8.60 wt.-% of saturated $C_{13}$
4.45 wt.-% of saturated $C_{15}$
0.02 wt.-% of monounsaturated $C_{15}$
0.20 wt.-% of bisunsaturated $C_{15}$
1.25 wt.-% of saturated $C_{17}$
19.10 wt.-% of monounsaturated $C_{17}$
28.5 wt.-% bisunsaturated $C_{17}$
0.60 wt.-% trisunsaturated $C_{17}$
0.05 wt.-% saturated $C_{19}$
1.25 wt.-% monounsaturated $C_{19}$
4.3 wt.-% others
Component b:
25 wt.-% N-oleoylsarcosine
Composition 6:
Component a:
84 wt.-% of a mixture of 1 weight part of distilled coconut fatty acid and 1 weight part of tall oil fatty acid with a hydrocarbon chain distribution as follows:
3.25 wt.-% of saturated $C_7$ hydrocarbon chain
2.85 wt.-% of saturated $C_9$
25.65 wt.-% of saturated $C_{11}$
8.60 wt.-% of saturated $C_{13}$
4.45 wt.-% of saturated $C_{15}$
0.02 wt.-% of monounsaturated $C_{15}$
0.20 wt.-% of bisunsaturated $C_{15}$
1.25 wt.-% of saturated $C_{17}$
19.10 wt.-% of monounsaturated $C_{17}$
28.5 wt.-% bisunsaturated $C_{17}$
0.60 wt.-% trisunsaturated $C_{17}$
0.05 wt.-% saturated $C_{19}$
1.25 wt.-% monounsaturated $C_{19}$
4.3 wt.-% others
Component b:
16 wt.-% N-oleoylsarcosine
3. Comparative Collector Compositions Composition 7:
80 wt.-% of tall oil fatty acid with a hydrocarbon chain distribution as follows:
0 wt.-% of saturated $C_7$ hydrocarbon chain
0 wt.-% of saturated $C_9$
0 wt.-% of saturated $C_{11}$
0 wt.-% of saturated $C_{13}$
0.30 wt.-% of saturated $C_{15}$
0.05 wt.-% of monounsaturated $C_{15}$
0.40 wt.-% of bisunsaturated $C_{15}$
1.10 wt.-% of saturated $C_{17}$
30.30 wt.-% of monounsaturated $C_{17}$
55.80 wt.-% bisunsaturated $C_{17}$
1.20 wt.-% trisunsaturated $C_{17}$
0 wt.-% saturated $C_{19}$
2.50 wt.-% monounsaturated $C_{19}$
8.50 wt.-% others
and
20 wt.-% N-oleoylsarcosine
Composition 8:
80 wt.-% of distilled coconut fatty acid with a hydrocarbon chain distribution as follows:
6.50 wt.-% of saturated $C_7$ hydrocarbon chain
5.70 wt.-% of saturated $C_9$
51.30 wt.-% of saturated $C_{11}$
17.20 wt.-% of saturated $C_{13}$
8.60 wt.-% of saturated $C_{15}$
0 wt.-% of monounsaturated $C_{15}$
0 wt.-% of bisunsaturated $C_{15}$
1.40 wt.-% of saturated $C_{17}$
7.90 wt.-% of monounsaturated $C_{17}$
1.20 wt.-% bisunsaturated $C_{17}$
0 wt.-% trisunsaturated $C_{17}$
0.10 wt.-% saturated $C_{19}$
0 wt.-% monounsaturated $C_{19}$
0.10 wt.-% others
and
20 wt.-% N-oleoylsarcosine
Composition 9:
100 wt.-% of tall oil fatty acid with a hydrocarbon chain distribution as follows:
0 wt.-% of saturated $C_7$ hydrocarbon chain
0 wt.-% of saturated $C_9$
0 wt.-% of saturated $C_{11}$
0 wt.-% of saturated $C_{13}$
0.30 wt.-% of saturated $C_{15}$
0.05 wt.-% of monounsaturated $C_{15}$
0.40 wt.-% of bisunsaturated $C_{15}$
1.10 wt.-% of saturated $C_{17}$
30.30 wt.-% of monounsaturated $C_{17}$
55.80 wt.-% bisunsaturated $C_{17}$
1.20 wt.-% trisunsaturated $C_{17}$
0 wt.-% saturated $C_{19}$
2.50 wt.-% monounsaturated $C_{19}$
8.50 wt.-% others
Composition 10:
100 wt.-% of a mixture of 1 weight part of distilled coconut fatty acid and 1 weight part of tall oil fatty acid with a hydrocarbon chain distribution as follows:
3.25 wt.-% of saturated $C_7$ hydrocarbon chain
2.85 wt.-% of saturated $C_9$
25.65 wt.-% of saturated $C_{11}$
8.60 wt.-% of saturated $C_{13}$
4.45 wt.-% of saturated $C_{15}$
0.02 wt.-% of monounsaturated $C_{15}$
0.20 wt.-% of bisunsaturated $C_{15}$
1.25 wt.-% of saturated $C_{17}$ 19.10 wt.-% of monounsaturated $C_{17}$
28.5 wt.-% bisunsaturated $C_{17}$
0.60 wt.-% trisunsaturated $C_{17}$
0.05 wt.-% saturated $C_{19}$
1.25 wt.-% monounsaturated $C_{19}$
4.3 wt.-% others 4. Flotation Test Results Example I: Apatite Ore Containing 16.1% $P_2O_5$, 47.9% $SiO_2$, 21.4% CaO, and 0.7% MgO A 390 g portion of the ore sample was ground in a laboratory stainless steel mill for 5 minutes at 50 rpm and 66% solids. This resulted in the following particle size distribution for the flotation feed: $P_{50}$=17 μm and $P_{80}$=47 μm. On completion of the grinding stage, the milled slurry was transferred to a 2.5 L capacity flotation cell, where the percentage solid was adjusted to approximately 15% by addition of the appropriate amount of water. The flotation device was a Denver D-12 flotation machine and the impeller speed set to 1100 rpm. The flotation pulp was thereafter conditioned for 4 minutes and 3 minutes with the depressants sodium silicate ($Na_2SiO_3$, 550 g/t) and sodium carbonate ($Na_2CO_3$, 280 g/t) respectively—in the indicated order. Next the collector mixture, which was freshly prepared as a 1% solution prior to starting each flotation test, was added and conditioned with the flotation pulp for 3 min. Finally, the air flow rate was set to 2 L/min and the resulting froth collected for 12 minutes.

| Collector com- position | Coconut oil fatty acid (wt.-%) | Tall oil fatty acid (wt.-%) | N-Oleoyl sarcosine (wt.-%) | Dosage (g/ton) | Grade $P_2O_5$ (wt.-%) | Recovery $P_2O_5$ (wt.-%) |
| --- | --- | --- | --- | --- | --- | --- |
| 1 | 40 | 40 | 20 | 500 | 27.86 | 55.74 |
| 2 | 20 | 60 | 20 | 500 | 25.47 | 69.57 |
| 3 | 50 | 30 | 20 | 500 | 27.77 | 58.35 |
| 7 (C) | — | 80 | 20 | 500 | 26.56 | 54.37 |
| 8 (C) | 80 | — | 20 | 500 | 30.82 | 42.91 |

The results from the flotation tests show that the collector compositions according to this invention (1 to 3) show excellent flotation efficiency and in particular, notably improved mineral recovery in comparison with the reference compositions 7 and 8.

The $P_2O_5$ grade obtained with the inventive compositions is slightly lower than what was obtained especially with the reference 8 in the laboratory experiments. This difference in grade is considered negligible because industrial flotation plants typically put the rougher concentrate through two, three or even four cleaning steps. In this way, the grade of the final concentrate is typically increased.

Example II: Ilmenite Ore Containing on Approximately 32% $TiO_2$

Approximately 1.2 L of sample was collected from the flotation feed stream of an ilmenite flotation plant. The 1.2 L sample, which consisted of approximately 1785 g dry ore and 750 g water, was thereafter transferred to a 3.2 L capacity flotation cell. The collector was thereafter added as-is and conditioned for 10 minutes using a Denver D-12 flotation device with the impeller speed set at 1550 rpm. The percentage solids in the slurry was thereafter reduced from 71% to 51% by addition of 1.0 L of industrial water. Hereafter, the air flow rate was set to 8.5 L/min and resulting froth collected for 270 seconds. In the case of the ore in question, a fatty acid and paraffin was used as collector combination. The results are shown below.

| Collector composition | Coconut oil fatty acid (wt.-%) | Tall oil fatty acid (wt.-%) | N-Oleoyl sarcosine (wt.-%) | Collector dosage (g/ton) | Paraffin dosage (g/ton) | Grade $TiO_2$ (wt.-%) | Recovery $TiO_2$ (wt.-%) |
| --- | --- | --- | --- | --- | --- | --- | --- |
| 1 | 40 | 40 | 20 | 840 | 360 | 37.4 | 81.1 |
| 9 (C) | — | 100 | — | 840 | 360 | 36.8 | 76.0 |

The flotation results show that a 1:1 replacement of the fatty acid collector resulted in a 5.1% increase in recovery in combination with a marginal increase in concentrate grade.

Example III: Scheelite Ore Containing 0.20% $WO_3$

The ground ore was conditioned with the depressants tannin (25 g/t), sodium silicate (350 g/t) and sodium carbonate (1000 g/t) after which the slurry pH was adjusted to pH 10 by adding the required amount of NaOH solution. The collector was then added as-is and conditioned with the flotation slurry for 2 minutes followed by addition of Clariant frother Flotanol 7026 and conditioning for a further 1 minute. Hereafter sufficient water was added to decrease the percentage solids in the flotation cell from 60% during the conditioning step to 35% in the flotation step. The air flow rate was now set to 5 L/min and the resulting froth collected for 2 minutes.

| Collector composition | Coconut oil fatty acid (wt.-%) | Tall oil fatty acid (wt.-%) | N-Oleoyl sarcosine (wt.-%) | Dosage (g/ton) | Grade $W_2O_3$ (wt.-%) | Recovery $W_2O_3$ (wt.-%) |
| --- | --- | --- | --- | --- | --- | --- |
| 4 | 33.5 | 33.5 | 33 | 145 | 1.16 | 78.3 |
| 5 | 37.5 | 37.5 | 25 | 194 | 0.81 | 84.2 |
| 6 | 42 | 42 | 16 | 151 | 1.61 | 78.0 |
| 10 (C) | 50 | 50 | — | 195 | 1.42 | 72.7 |
| 9 (C) | — | 100 | — | 184 | 0.87 | 71.3 |
| 9 (C) | — | 100 | — | 369 | 0.72 | 78.2 |

The use of the new collector mixture resulted in a significant increase in $WO_3$ grade as compared to the comparative product (100% tall oil fatty acid collector). In addition, a similar $WO_3$ recovery value was obtained with 151 g/t dosage of the new collector blend as compared with 369 g/t dosage of the comparative tall oil fatty acid collector.

The invention claimed is:
1. A collector composition for the direct froth flotation of nonsulfide ores comprising
   a) 50-99 wt.-% of a mixture of fatty acids and
   b) 1-50 wt.-% of an N-acyl derivative of sarcosine of the formula (I)

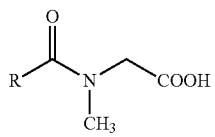

wherein
R is a saturated or unsaturated hydrocarbon chain with 7 to 21 carbon atoms, wherein the mixture of fatty acids comprises 10.0-35.0 wt.-% of fatty acid having a saturated $C_{11}$ hydrocarbon group, 2.5-15.0 wt.-% of fatty acid having a saturated $C_{13}$ hydrocarbon group, 10.0-25.0 wt.-% fatty acid having a monounsaturated $C_{17}$ hydrocarbon group and 20.0-45.0 wt.-% fatty acid having a bisunsaturated $C_{17}$ hydrocarbon group.

2. The collector composition according to claim 1, wherein the fatty acid mixture comprises fatty acids having
1.0-6.5 wt.-% of saturated $C_7$ hydrocarbon chain
1.0-4.0 wt.-% of saturated $C_9$
10.0-35.0 wt.-% of saturated $C_{11}$
2.5-15.0 wt.-% of saturated $C_{13}$
1.0-7.0 wt.-% of saturated $C_{15}$
0.0-1.0 wt.-% of monounsaturated $C_{15}$
0.0-1.0 wt.-% of bisunsaturated $C_{15}$
0.5-2.0 wt.-% of saturated $C_{17}$
10.0-25.0 wt.-% of monounsaturated $C_{17}$
20.0-45.0 wt.-% bisunsaturated $C_{17}$
0.0-2.0 wt.-% trisunsaturated $C_{17}$
0.0-1.0 wt.-% saturated $C_{19}$
0.0-4.0 wt.-% monounsaturated $C_{19}$, and
0.0-7.0 wt.-% other fatty acids.

3. The composition of claim 1, wherein component a) is a mixture of 0.3 to 1.7 weight parts of coconut oil fatty acid to 1 weight part of tall oil fatty acid.

4. The composition of claim 1, wherein the component b) is N-oleoylsarcosine.

5. The composition as claimed in claim 1, wherein the component a) is 80 wt.-% of a mixture of 1 weight part of coconut oil fatty acid and 1 weight part of tall oil fatty acid and component b) is 20 wt.-% of N-oleoylsarcosine.

6. A process for the direct froth flotation of at least one nonsulfide mineral, the process comprising the steps of bringing a collector composition comprising
a) 50-99 wt.-% of a mixture of fatty acids and
b) 1-50 wt.-% of an N-acyl derivative of sarcosine of the formula (I)

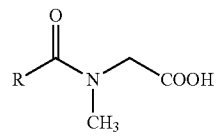

wherein
R is a saturated or unsaturated hydrocarbon chain with 7 to 21 carbon atoms, wherein the mixture of fatty acids comprises 10.0-35.0 wt.-% of fatty acid having a saturated $C_{11}$ hydrocarbon group, 2.5-15.0 wt.-% of fatty acid having a saturated $C_{13}$ hydrocarbon group, 10.0-25.0 wt.-% fatty acid having a monounsaturated $C_{17}$ hydrocarbon group and 20.0-45.0 wt.-% fatty acid having a bisunsaturated $C_{17}$ hydrocarbon group, in contact with an aqueous suspension of the nonsulfide mineral to form a mineral pulp, and frothing the mineral pulp.

7. The process as claimed in claim 6, wherein the nonsulfide mineral is apatite.

8. The process as claimed in claim 6, wherein the nonsulfide mineral is selected from the group of calcite, scheelite, fluorspar, magnesite and barite.

9. The process as claimed in claim 6, wherein the nonsulfide mineral is ilmenite.

10. A direct froth flotation process according to claim 6, wherein the amount of collector composition added is an amount between 100 g and 1000 g per ton of ore.

* * * * *